United States Patent
Yokota et al.

(10) Patent No.: US 6,368,479 B1
(45) Date of Patent: Apr. 9, 2002

(54) CARBON MONOXIDE SENSOR, METHOD FOR MAKING THE SAME, AND METHOD OF USING THE SAME

(75) Inventors: Minoru Yokota, Okazaki; Takao Murase, Kohnan, both of (JP)

(73) Assignee: NGK Insulators Ltd. (JP)

( * ) Notice: Subject to any disclaimer, the term of this patent is extended or adjusted under 35 U.S.C. 154(b) by 0 days.

(21) Appl. No.: 09/361,115

(22) Filed: Jul. 27, 1999

(30) Foreign Application Priority Data

Aug. 25, 1998 (JP) ............................................ 10-238552

(51) Int. Cl.$^7$ ............................................ G01N 27/407
(52) U.S. Cl. ........................ 204/424; 204/425; 204/427
(58) Field of Search ................ 204/424–429; 205/783.5, 784, 784.5, 786.5

(56) References Cited

U.S. PATENT DOCUMENTS

| | | | | |
|---|---|---|---|---|
| 3,843,400 A | * | 10/1974 | Radford et al. ............. | 204/424 |
| 3,914,169 A | * | 10/1975 | Horowitz .................... | 204/424 |
| 4,498,968 A | * | 2/1985 | Yamada et al. ............. | 204/412 |
| 4,828,673 A | * | 5/1989 | Maeda ........................ | 204/427 |
| 5,902,469 A | * | 5/1989 | Kato et al. .................. | 204/425 |
| 4,985,126 A | * | 1/1991 | Haefele et al. ............. | 204/406 |
| 5,296,112 A | * | 3/1994 | Seger et al. ................ | 204/424 |
| 5,348,574 A | | 9/1994 | Tokas et al. | |
| 5,397,442 A | | 3/1995 | Wachsman | |
| 5,630,920 A | * | 5/1997 | Friese et al. ................ | 204/424 |
| 5,667,652 A | | 9/1997 | Liu et al. | |
| 5,763,763 A | * | 6/1998 | Kato et al. .................. | 73/23.32 |
| 5,766,433 A | * | 6/1998 | Can et al. ................... | 204/421 |

FOREIGN PATENT DOCUMENTS

| | | |
|---|---|---|
| DE | 44 42 272 A1 | 5/1996 |
| EP | 0 797 095 A2 | 9/1997 |
| EP | 0 851 226 A2 | 7/1998 |
| GB | 2 288 873 A | 11/1995 |
| JP | 4-14302 | 3/1992 |
| JP | 7-248309 | 9/1995 |
| JP | 8-189914 | 7/1996 |
| JP | 10-104197 | 4/1998 |

OTHER PUBLICATIONS

Lukacs et al., "Electrochemical investigations of a carbon monoxide–oxygen sensor", Solid State Ionics 68, pp. 93–98, 1994.*

Chiou et al., "Amperometric sulfur dioxide sensors using the gold deposited gas–diffusion electrode", Electroanalysis, 8, pp. 1179–1182 (CAS abstract only), 1994.*

Chiou et al., Amperometric sulfur dioxide sensors using the gold deposited gas–diffusion electrode, Electroanalysis, 8, 1996, pp. 1179–1182.*

* cited by examiner

Primary Examiner—Robert J. Warden, Sr.
Assistant Examiner—Kaj K. Olsen
(74) Attorney, Agent, or Firm—Parkhurst & Wendell L.L.P.

(57) ABSTRACT

Provided is a CO sensor which comprises a solid electrolyte 11 having oxygen ion conductivity and a standard electrode 15 and a sensing electrode 16 for measurement of carbon monoxide and at least one standard electrode 15 and sensing electrode 17 for measurement of at least one different gas other than carbon monoxide, especially sulfur dioxide, these electrodes being formed on at least a part of the surface of the solid electrolyte 11. This CO sensor is excellent in selectivity for carbon monoxide, can exclude the influence of the coexisting sulfur dioxide and oxygen on the carbon monoxide measured value, and, besides, can be used at high temperatures. A method for making the sensor and a method of using it are also provided.

22 Claims, 4 Drawing Sheets

CARBON MONOXIDE SENSOR, METHOD FOR MAKING THE SAME, AND METHOD OF USING THE SAME

FIELD OF THE INVENTION AND DESCRIPTION OF RELATED ART

The present invention relates to a CO sensor for measuring a concentration of carbon monoxide (CO) contained in an exhaustion gas such as from combustion engines and the like, and more particularly to a CO gas sensor which is operable at high temperatures with excluding effects of coexisting sulfur dioxide ($SO_2$) and oxygen ($O_2$) on CO measurement values, and a method for making the sensor and a method of using the sensor.

In boilers for thermal-power generation (oil fired boilers, LNG fired boilers, coal fired boilers, etc.) and incineration equipment, it is desired to inhibit incomplete combustion and reduce the amount of harmful CO discharged into the air. Therefore, sensors for detecting generation of CO and measuring the concentration of CO have hitherto been disposed in the above equipment.

As examples of the main CO sensors, mention may be made of semiconductor type, catalyst combustion type, solid electrolyte type, and thermal transfer type. Among them, the solid electrolyte type CO sensors utilize measurement of the electromotive force of a concentration cell as a principle of measurement, and it comprises a metal electrode and a stabilized zirconia having oxygen ion conductivity and is superior in heat resistance, shock resistance and poisoning resistance.

Furthermore, since exhaustion gases from various equipment such as boilers for thermal-power generation contain harmful components such as $NO_x$ and $SO_2$, a duty is imposed in the equipment to monitor the concentrations of these harmful gases in the exhaustion gas, and a non-dispersion infrared absorption type (NDIR type) measurement apparatus is mainly used for these gases. This apparatus is not directly inserted in the exhaustion gas, but the exhaustion gas is subjected to sampling by an absorption pump and analysis is conducted at a place at a distance from a gas flue (passage of exhaustion gas)

The CO sensors using the stabilized zirconia sense CO utilizing the oxidation reaction of CO, and in case the detection gas contains gases such as $SO_2$, these gases are also further oxidized and sensed. Thus, there is the problem that accuracy for the measurement of CO concentration is lowered. Although detection sensitivity for $SO_2$ and others is lower than that for CO, if the concentrations of these gases increase, measurement error increases. Therefore, in order to perform a precise measurement of CO concentration, the measurement Aceq value of CO must be corrected based on the information obtained from the NDIR type sensor.

However, measurement using these different sensors is inconvenient in installation of the apparatuses, maintenance and inspection, and data processing. In the case of NDIR type sensor, there are further problems that a time lag is caused by collection and analysis of gas, and precision of measurement is lowered due to the influence by other gases such as CO, carbon dioxide ($CO_2$) and hydrocarbons (HC). Of course, there is a problem of being affected by $NO_x$ or $SO_2$ when CO is measured by NDIR.

Furthermore, the solid electrolyte type CO sensor suffers from the further problem that since platinum is used as an electrode material, it also works as an oxygen ($O_2$) sensor, and the CO concentration cannot be selectively measured for the gas in which $O_2$ coexists. In this case, at high temperatures of 600–900° C., the oxidation reaction of CO rapidly proceeds on the surface of the platinum electrode, and when oxygen is contained in the gas to be measured, it is difficult to distinguish the measurement results attributable to oxygen and CO from each other.

SUMMARY OF THE INVENTION

The present invention has been accomplished in an attempt to solve the problems in the conventional techniques, and the object is to provide a CO sensor using a solid electrolyte for precise measurement of CO concentration which simultaneously carries out measurement of the concentration of $SO_2$ and/or $O_2$ which are especially liable to cause measurement error while excluding the influence of $SO_2$ or $O_2$.

That is, according to the present invention, there is provided a carbon monoxide sensor comprising a solid electrolyte having oxygen ion conductivity, a standard electrode and a sensing electrode for measurement of carbon monoxide, and one or more standard electrodes and sensing electrodes for measurement of one or more different gases other than carbon monoxide, said standard electrodes and sensing electrodes being formed on at least a part of the surface of the solid electrolyte, characterized in that one of the different gases is sulfur dioxide.

Furthermore, according to the present invention, there is provided a method for making a carbon monoxide sensor which comprises a bottomed cylindrical or rod-like solid electrolyte having an electrode on the outer surface of the bottom portion and provided with at least one bottomed hole at the bottom portion inside the electrolyte, an electrode being provided on the inner surface of the bottomed hole, characterized in that the bottom portion of the solid electrolyte is dipped in an organic metal solution containing Au or a component of Au alloy and/or a component of the solid electrolyte, and/or the organic metal solution is poured into the bottomed hole and sucked out therefrom to coat the inner surface of the bottomed hole with the solution, followed by firing to form the electrodes.

According to the method for making a carbon monoxide sensor of the present invention, not only the production cost can be reduced by a simple production method depending on the shape of the desired carbon monoxide sensor, but also the quality of the sensor produced can be maintained at constant.

Furthermore, the present invention provides a method of using a carbon monoxide sensor for measurement of carbon monoxide concentration, said carbon monoxide sensor comprising standard electrodes and sensing electrodes for measurement of carbon monoxide concentration and for measurement of sulfur dioxide concentration, respectively, and/or reference electrodes for measurement of carbon monoxide concentration and for measurement of sulfur dioxide concentration, respectively, and/or a standard electrode for measurement of oxygen concentration, and/or a sensing electrode for measurement of oxygen concentration which are formed on at least a part of the surface of a solid electrolyte having oxygen ion conductivity, characterized in that the carbon monoxide concentration and the sulfur dioxide concentration are simultaneously measured, and the carbon monoxide concentration is determined by correcting the result of measurement of the carbon monoxide concentration using the result of measurement of the sulfur dioxide concentration.

As a suitable method, mention may be made of a method in which the carbon monoxide concentration is measured by measuring change in electromotive force between the sensing electrode and the standard electrode and/or change in electromotive force between the sensing electrode and the reference electrode which are caused by adsorption/oxidation of carbon monoxide when a constant current is allowed to flow between the sensing electrode and the standard electrode for measurement of carbon monoxide, and the sulfur dioxide concentration is measured by measuring change in electromotive force between the sensing electrode and the standard electrode and/or change in electromotive force between the sensing electrode and the reference electrode which are caused by adsorption/oxidation of sulfur dioxide when a constant current is allowed to flow between the sensing electrode and the standard electrode for measurement of the sulfur dioxide concentration.

DESCRIPTION OF THE PREFERRED EMBODIMENTS OF THE INVENTION

Figure 1:
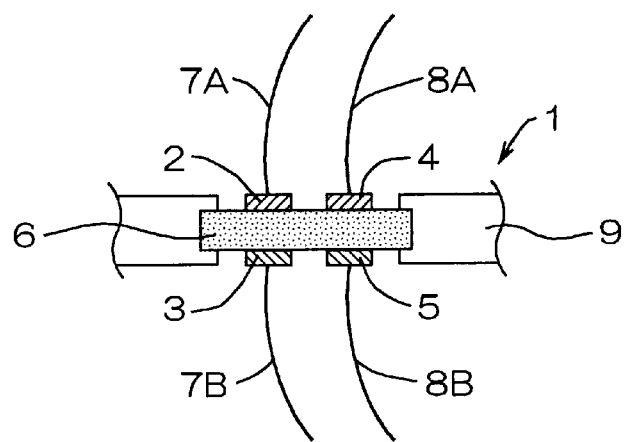
FIG. 1 is a sectional view showing a basic structure of the CO sensor according to the present invention.

In the carbon monoxide sensor of the present invention, it is preferred to use gold or a gold alloy excellent in selectivity for CO as the sensing electrode for the measurement of carbon monoxide, and it is also preferred to use a cermet electrode composed of gold or a gold alloy and the same material as of the solid electrolyte. These sensing electrode and/or standard electrode can be simply formed by coating an organic metal solution containing gold or a component of gold alloy and/or a component of the solid electrolyte, followed by firing. A reference electrode for the measurement of carbon monoxide may be provided in combination.

On the other hand, as a sensing electrode for measurement of sulfur dioxide provided in combination in the carbon monoxide sensor, preferably, gold or a gold alloy and a glass component are used in combination, and preferably a reference electrode for measurement of sulfur dioxide is further provided in combination. Here, as preferred glass components, mention may be made of, for example, borosilicate glass, lead borosilicate glass, and lead borate glass.

The standard electrode for measurement of carbon monoxide and the standard electrode for measurement of sulfur dioxide can be commonly used as one electrode. Moreover, when a sensing electrode and/or a standard electrode are provided so as to be able to measure oxygen as another different gas, the measurement precision can further be improved and this is preferred.

Furthermore, in the carbon monoxide sensor, it is also preferred to provide a gas diffusion regulating layer on the surface of the sensing electrode for measurement of carbon monoxide and/or measurement of sulfur dioxide, and in case oxygen is sensed, correction of concentration of oxygen can be more precisely performed by providing an oxygen pump cell for control of oxygen concentration in the measuring atmosphere. As an electrode for the oxygen pump cell, it is preferred to use a metal oxide.

The solid electrolyte used in the carbon monoxide sensor preferably comprises zirconium oxide and a stabilizer. As the stabilizer, suitable is at least one compound selected from magnesium oxide, calcium oxide, yttrium oxide, cerium oxide, scandium oxide, and rare earth metal oxides. If an electrical heater is disposed in the solid electrolyte, the working temperature of the sensor can be controlled and this is preferred.

As for the shape of the carbon monoxide sensor of the present invention, when the solid electrolyte is in the form of a bottomed cylinder, and a standard electrode and/or a reference electrode for measurement of carbon monoxide and for measurement of different gas are formed on the outer surface of the bottom portion, furthermore at least two bottomed holes are formed in the inside bottom portion, and a sensing electrode for measurement of carbon monoxide and a sensing electrode for measurement of the different gas are formed on the inner surface of the respective bottomed holes, the production of the sensor is easy and besides separation between the standard gas and the gas to be measured becomes easy, and thus the sensor is easy in use and, besides, can be made to a compact shape. In addition, in such construction, the solid electrolyte may be formed in the form of a rod, and the bottomed holes may be formed in the lengthwise direction and the electrodes may be similarly formed.

Conversely, when the solid electrolyte is in the form of a bottomed cylinder, and sensing electrodes for measurement of carbon monoxide and for measurement of different gas are formed on the outer surface of the bottom portion, at least one bottomed hole is formed in the inside bottom portion, and a standard electrode and/or a reference electrode for measurement of carbon monoxide and for measurement for different gas are formed on the inner surface of the respective bottomed holes, the similar effect can also be obtained. In this case, too, the solid electrolyte may be formed in the form of a rod, and the bottomed holes may be formed in the lengthwise direction and the electrodes may be similarly formed. Moreover, it is also preferred that the solid electrolyte is in the form of a bottomed cylinder, and a recess is provided on the outer surface of the bottom portion, a sensing electrode for measurement of carbon monoxide is formed in the recess, a sensing electrode for measurement of different gas is formed on the outer surface of the bottom portion of the solid electrolyte, and a standard electrode and/or a reference electrode for measurement of carbon monoxide and for measurement for different gas are formed on the inner surface of the bottom portion of the solid electrolyte. It is a matter of course that such structures of carbon monoxide sensor of the present invention can be applied to other gas sensors.

Furthermore, preferred are a method of measuring carbon monoxide concentration by measuring a current value between the sensing electrode and the standard electrode and/or a current value between the sensing electrode and the reference electrode upon oxidation of carbon monoxide when a constant voltage is kept between the sensing electrode and the standard electrode for measurement of carbon monoxide, and a method of measuring sulfur dioxide concentration by measuring a current value between the sensing electrode and the standard electrode and/or a current value between the sensing electrode and the reference electrode upon oxidation reaction of sulfur dioxide when a constant voltage is kept between the sensing electrode and the standard electrode for measurement of sulfur dioxide. In these using methods (measuring methods), when oxygen concentration is further measured, and the results of measurement of carbon monoxide concentration and sulfur dioxide concentration are corrected by the result of measurement of oxygen concentration, the measurement precision is further enhanced and this is preferred. The carbon monoxide sensor can be suitably used at a temperature of the solid electrolyte in the range of 600–900° C.

As mentioned above, in the case of measuring the concentration of CO contained in exhaustion gases such as from combustion engines, present invention has advantages that the concentration of CO can be precisely measured in one sensor with easily excluding effects of the coexisting $SO_2$ or $O_2$.

The modes for carrying out the present invention will be explained referring to the accompanying drawings, but they never restrict the present invention.

FIG. 1 is a sectional view which shows the basic structure of the CO sensor of the present invention. The CO sensor 1 is a CO sensor which comprises a standard electrode 2 for measurement of CO (hereinafter referred to as "CO standard electrode") and a sensing electrode 3 for measurement of CO (hereinafter referred to as "CO sensing electrode"), and at least one standard electrode 4 and sensing electrode 5 for measurement of at least one different gas other than CO, said electrodes being formed on at least one portion of the surface of a solid electrolyte 6 having oxygen ion conductivity. In the present invention, sulfur dioxide is selected at least the different gas here. Accordingly, the standard electrode 4 and the sensing electrode 5 are hereinafter referred to as $SO_2$ standard electrode 4 and $SO_2$ sensing electrode, respectively.

The standard electrodes 2 and 4 are formed on the side of the standard gas and the sensing electrodes 3 and 5 are formed on the side of the gas to be measured, and lead wires 7A and 8A, and 7B and 8B are connected to the respective electrodes. In this case, the standard electrodes 2 and 4 may be formed as one standard electrode, and one lead wire may be connected to this standard electrode. The solid electrolyte 6 is fitted into a gas impermeable substrate 9 and also serves as a partition which separates the area of the gas to be measured and the area of the standard gas from each other.

The solid electrolyte 6 can be a material having oxygen ion conductivity, and examples of the material are zirconium oxide, bismuth oxide, and cerium oxide. In the present invention, stabilized zirconia superior in high-temperature stability and chemical stability can be suitably used. As stabilizers, preferred are magnesium oxide (MgO), calcium oxide (CaO), yttrium oxide ($Y_2O_3$), cerium oxide ($CeO_2$), scandium oxide ($Sc_2O_3$), and rare earth element oxides.

As the solid electrolyte 6, a molded body of a given shape can be obtained by various known methods, e.g., press molding method, cast molding method, or extrusion molding method, or by subjecting to punching process a green sheet made by doctor blade method. The resulting molded bodies are degreased and fired to obtain the solid electrolytes. If necessary, the products may further be subjected to grinding and abrasion. Moreover, the surface may be roughened by chemical etching, for example, by immersing them in a 2.5% hydrofluoric acid solution for 20–30 minutes.

The standard electrodes 2 and 4 are electrically and mechanically connected to the solid electrolyte 6, and they are preferably porous because they are required to have a function as electrodes which diffuse/adsorb a gas. Since the standard electrodes 2 and 4 are also the sites of electrochemical reaction of ionizing $O_2$ in the standard gas, the material suitable for them is platinum (Pt) which adsorbs and ionizes $O_2$. Moreover, there may be used alloys mainly composed of Pt with palladium (Pd), rhodium (Rd) or the like or cermet materials of Pt or Pt alloys with solid electrolyte materials.

The reason for using cermet as a material of the standard electrodes 2 and 4 is as follows. Since the electrochemical reaction of ionizing $O_2$ in the standard gas takes place at the contact interface of the three of the gas phase, the metal electrode and the solid electrolyte, many sites for this reaction should be provided, and peeling of the electrodes caused when used at high temperatures should be prevented by improving adhesion between the electrodes and the solid electrolyte and by matching the thermal expansion coefficients.

For simple and easy connection of the standard electrodes 2 and 4 to the solid electrolyte 6, there may be employed a method which comprises printing a paste containing Pt or a paste comprising a cermet of Pt and the solid electrolyte on the surface of the solid electrolyte 6 by screen printing or the like and baking the printed paste by applying a Pt mesh to the undried paste and then drying it or a method which comprises impregnating a Pt mesh with a slurry containing Pt, then disposing the mesh on the solid electrolyte 6 in the state of the slurry being undried, and baking the slurry. Alternatively, the paste may be left in the state as screen printed. The baking may be carried out simultaneously with baking of the sensing electrodes 3 and 5 or may be carried out separately and one after another.

The lead wires 7A and 8A are suitably Pt wires, and for the connection to the standard electrodes 2 and 4, in the case of using a Pt mesh for the standard electrodes 2 and 4, a method of previously welding the lead wires 7A and 8A to the Pt mesh by spot welding, arc welding or the like is preferred because a high bond strength can be obtained. When the electrodes are formed only by screen printing, the lead wires 7A and 8A can be connected to the electrodes by baking. Other methods for the formation of electrodes include Pt plating, baking of a platinum chloride film, and others.

On the other hand, the sensing electrodes 3 and 5 are also electrically and mechanically connected to the solid electrolyte 6 in the same manner as the connection of the standard electrodes 2 and 4, and the sensing electrodes 3 and 5 are preferably porous since they are required to have a function of allowing an oxidation reaction to take place between oxygen ions which has moved through the solid electrolyte and a gas to be measured which is adsorbed to the metal component of the electrodes at the contact interface of the three of gas phase/metal electrode/solid electrolyte and a function of releasing the gas produced.

As the material of the CO sensing electrode 3, preferred is one which has a property not to accelerate the oxidation of CO with the coexisting $O_2$. That is, it is preferred that the reaction between adsorbed oxygen (O(ad)) and CO as shown in the following formula (I) does not take place, but oxygen ion ($O_2{}^-$) which has moved from the side of the CO standard electrode 2 through the solid electrolyte 6 reacts with CO to produce $CO_2$ and electron ($e^{31}$) as shown in the following formula (II). The produced electron is applied for the measurement of CO concentration.

$$CO+O\ (ad)\rightarrow CO_2 \qquad (I)$$

$$CO+O^{2-}\rightarrow CO_2+2e^- \qquad (II)$$

Therefore, in the present invention, as the CO sensing electrode 3, gold (Au) or gold alloys (Au alloys) satisfactory in catalytic activity shown by the formula (II) can be suitably used. As the Au alloys, mention may be made of those which comprise Au and 0.1–10 wt %, preferably 0.1–5 wt %, more preferably 0.1–1 wt % of other noble metals such as Rh, Pt, Pd, and silver (Ag). By adding the other noble metals, agglomeration of Au particles at the time of making the CO sensing electrode 3 at high temperatures can be inhibited, and maintenance of porosity of the CO sensing electrode 3 and enlargement of the surface area become possible, and as a result, CO detection sensitivity can be further improved.

Furthermore, the CO sensing electrode 3 may be formed of a cermet electrode composed of Au or an Au alloy and the same material as of the solid electrolyte 6. In the cermet electrode, there are obtained the effects that the contact interface of the three of gas phase/metal electrode/solid electrolyte increases and chemical reaction readily takes place to result in increase of measurement sensitivity and besides enhancement of adhesion to the solid electrolyte 6, and as a result, the electrode is hardly peeled off.

Connection of the CO sensing electrode 3 to the solid electrolyte 6, and connection of lead wire 7B to the CO sensing electrode 3 can be performed using a paste containing Au, an Au alloy or a mixture of Au and the above-mentioned noble metal as electrode materials or a paste comprising a cerment of Au and the solid electrolyte, an Au mesh or an Au alloy mesh, and the lead wire 7B made of Au in the same manner as in the connection of the Co standard electrode 2 mentioned above.

Here, the CO sensing electrode 3 may be formed by forming a fine particle layer using fine particles of Au or an Au alloy, and forming an electrode film thereon. In this case, a paste in which fine particles are dispersed is coated on the solid electrolyte 6 and fired, and an electrode film comprising Au or an Au alloy is coated thereon and fired, or the fine particle layer and the electrode film are coated in succession and these are simultaneously fired. The fine particles of Au or an Au alloy are those of 0.01–10 $\mu$, preferably 0.01–1 $\mu$, more preferably 0.01–0.1 $\mu$ in average particle size, and the shape of the particles may not necessarily be spherical, and may be in the form of granules or Rugby balls. Other methods for the formation of the CO sensing electrode 3 include Au plating, sputtering and the like.

On the other hand, the $SO_2$ sensing electrode 5 also preferably has the property not to accelerate oxidation of $SO_2$ gas with the coexisting $O_2$. That is, it is preferred that the reaction between the adsorbed oxygen (O(ad)) and $SO_2$ gas as shown in the following formula (III) does not take place, but oxygen ion ($O^{2-}$) which has moved from the side of the $SO_2$ standard electrode 4 through the solid electrolyte 6 reacts with $SO_2$ gas to produce $SO_3$ and electron ($e^{31}$) as shown in the following formula (IV). The produced electron is applied for the measurement of $SO_2$ concentration.

$$SO_2+O\ (ad)\rightarrow SO_3 \qquad (III)$$

$$SO_2+O^{2-}\rightarrow SO_3+2e^- \qquad (IV)$$

Therefore, it is preferred to use Au or an Au alloy and a glass component in combination as the $SO_2$ sensing electrode 5. Au or an Au alloy is used as the metallic material because the reaction of the formula (IV) more readily takes place than the reaction of the formula (III). By using the glass component in combination and by precipitating a glass phase at the contact interface of the three of the gas phase, the metal electrode, and the solid electrolyte at the time of making the $SO_2$ sensing electrode 5, the reaction of combustible gases such as CO at the contact interface of the three can be inhibited. That is, measurement of precise concentration of $SO_2$ becomes possible. As the glass components, any of those which melts at lower than the melting point of gold or a gold alloy can be used, and, among them, borosilicate glass, lead borosilicate glass, and lead borate glass, and the like can be suitably used.

Amount of the glass component is preferably in the range of 1–10 wt % based on the total weight of Au or Au alloy and the glass component. If the amount of the glass component is less than 1%, improvement in adhesion between the solid electrolyte 6 and the $SO_2$ sensing electrode 5 is not recognized, and the effect to diminish the interference by combustible gases such as CO is not sufficient. If it exceeds 10%, the sensing performance is deteriorated.

The $SO_2$ sensing electrode 5 can be formed in the same manner as in the formation of the CO sensing electrode 3 comprising a cermet electrode. That is, mixed powders of Au or an Au alloy and a glass component are made pasty and the paste is coated on the solid electrolyte 6 and fired or the powders are dispersed in a suitable solvent and the dispersion is coated on the solid electrolyte 6 and fired. As Au or Au alloy powders used in this case may be the same as those used for the formation of the CO sensing electrode 3. The method of connection of lead wire 8B and materials thereof are also the same as in the connection of the lead wire 7B.

The solid electrolyte 6 to which various electrodes are connected in this way is fitted into substrate 9 so as to separate the standard gas atmosphere and the atmosphere of the gas to be measured from each other. Here, the solid electrolyte 6 and the substrate 9 can be sealed using a glass fusing material or the like. When such construction is employed, each of the standard electrodes 2 and 4 may be formed of the same material as each of the corresponding sensing electrodes 3 and 5. As the standard gas, air is ordinarily used.

In the case of such partition type structure, CO concentration and $SO_2$ concentration in the gas to be measured can be measured by measuring electromotive force due to the difference in CO partial pressure and $SO_2$ partial pressure of the standard gas and the gas to be measured, respectively. In this way, the CO concentration and the $SO_2$ concentration are simultaneously measured, and the measured value of the CO concentration is corrected using the measured value of the $SO_2$ concentration, whereby more precise CO concentration can be determined.

More specifically, mention may be made of the following method: namely, CO concentration is measured by measuring the change of electromotive force caused by adsorption/oxidation of CO when a constant electric current is passed between the CO sensing electrode 3 and the CO standard electrode 2, and $SO_2$ concentration is measured by measuring the change of electromotive force caused by adsorption/oxidation of $SO_2$ when a constant electric current is passed between the $SO_2$ sensing electrode 5 and the $SO_2$ standard electrode 4, and the CO measured value is corrected by the $SO_2$ measured value.

Another preferred method is as follows. That is, CO concentration is measured by measuring current value based on oxidation of CO when a constant voltage is kept between the CO sensing electrode 3 and the CO standard electrode 2, and $SO_2$ concentration is measured by measuring current value based on oxidation reaction of $SO_2$ when a constant voltage is kept between the $SO_2$ sensing electrode 5 and the $SO_2$ standard electrode 4, and from these results, the CO concentration is determined. The CO sensor 1 can be suitably used when the temperature of the solid electrolyte 6 is in the range of 600–900° C., and the various sensors exemplified below are also used under the same conditions.

Figure 2:
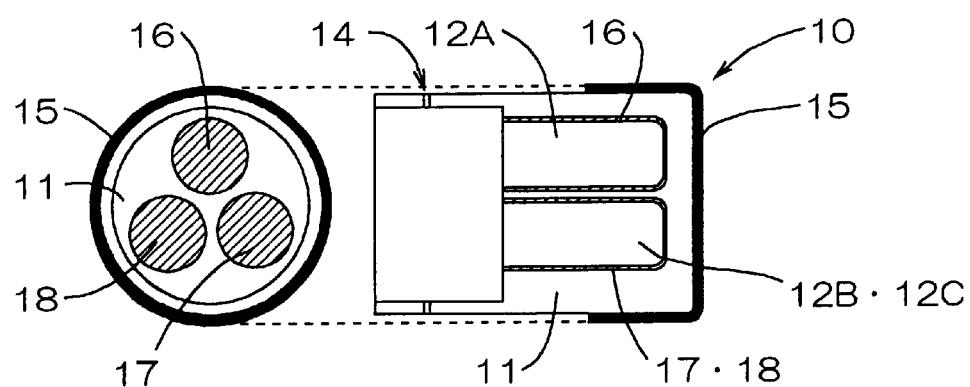
FIG. 2 is a sectional view showing one embodiment of the CO sensor according to the present invention.

FIG. 2 shows one embodiment of the CO sensors of the present invention. In the CO sensor 10, a standard electrode 15 for measurement of both $CO/SO_2$ (hereinafter referred to as "standard electrode 15" is formed on the outer surface of the bottom portion of a bottomed cylindrical solid electrolyte 11, three bottomed holes 12A, 12B and 12C are formed at the inner bottom portion of the solid electrolyte, and a CO sensing electrode 16 is formed on the inner surface of the bottomed hole 12A, a reference electrode 18 for measurement of CO (hereinafter referred to as "CO reference electrode) is formed on the inner surface of the bottomed hole 12C, and an $SO_2$ sensing electrode 17 is formed on the inner surface of the bottomed hole 12B. The bottomed holes 12A, 12B, and 12C have no limitation in their shapes.

Figure 3:
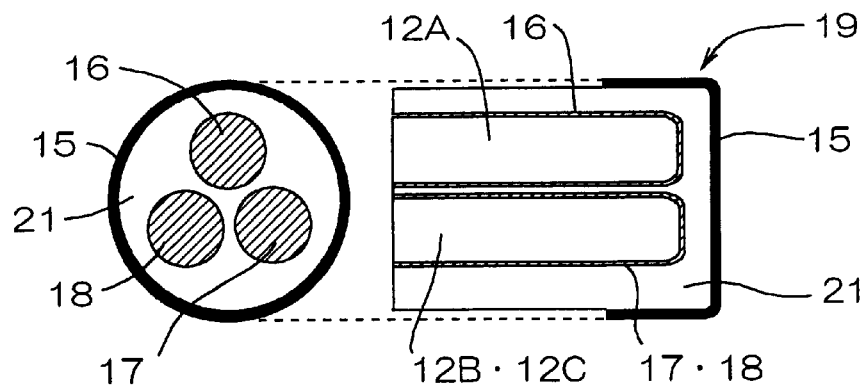
FIG. 3 is a sectional view showing another embodiment of the CO sensor according to the present invention.

FIG. 3 shows another embodiment of the CO sensors of the present invention. In the CO sensor 19, a solid electrolyte 21 is in the form of a rod, bottomed holes 12A, 12B and 12C are formed in the lengthwise direction of the solid electrolyte, and the construction of the electrodes is the same as in the CO sensor 10. Therefore, the CO sensor 10 and the CO sensor 19 differ only in the shape of the solid electrolyte, and explanation will be given below taking the CO sensor 10 as an example.

The CO reference electrode 18 is made of the same material as of the standard electrode 15, but this is not necessarily needed. On the other hand, a bottomed hole may be further provided in the CO sensor 10 to provide a reference electrode for measurement of $SO_2$. The $SO_2$ reference electrode in this case is made of the same material as of the $SO_2$ standard electrode. In addition, a sensing electrode for measurement of $O_2$ may be provided. In this way, in the CO sensor 10, the number of the bottomed holes can be optionally set depending on the number of the gases to be measured and the number of the electrodes to be provided, but two or more holes containing two of the CO sensing electrode 16 and the $SO_2$ sensing electrode 17 are necessary.

Furthermore, in the CO sensor 10, the standard electrode 15 performs both the roles of a CO standard electrode and an $SO_2$ standard electrode, but when the CO standard electrode and the $SO_2$ standard electrode are separately formed, the respective standard electrodes may be formed at the positions on the outer peripheral surface of the bottom portion which are near the respective sensing electrodes.

The lead wires (not shown) connected to the CO sensing electrode 16, the $SO_2$ sensing electrode 17, and the CO reference electrode 18 can be drawn out from a hole portion 14 provided at the solid electrolyte 11 into the outside of the cylinder. The space between the hole portion 14 and the lead wire is filled up with glass or a metal paste, and going in and out of a gas from inside and outside of the cylinder through the hole portion 14 can be prevented.

Figure 4:
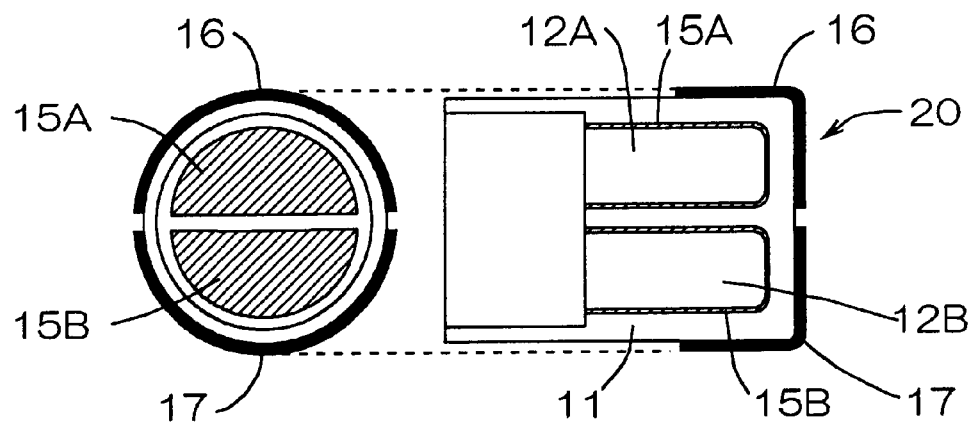
FIG. 4 is a sectional view showing still another embodiment of the CO sensor according to the present invention.

In addition to the structure where the standard electrode 15 is formed on the outer periphery as in the CO sensors 10 and 19, a CO sensing electrode 16 and an $SO_2$ sensing electrode 17 may be formed on the outer surface of the bottom portion, two bottomed holes 12A and 12B may be formed in the inner bottom portion, and a CO standard electrode 15A and an $SO_2$ standard electrode 15B may be formed on the inner surface of the respective bottomed holes 12A and 12B as in the CO sensor 20 shown in FIG. 4. In case the CO standard electrode 15A and the $SO_2$ standard electrode 15B are commonly used, the bottomed holes 12A and 12B may not be provided if the bottom portion of the solid electrolyte 11 is thinly formed.

When the shape of CO sensor is cylindrical or rod-like as shown in FIG. 2, FIG. 3 and FIG. 4, the CO sensors can be easily made, are easy in use because the standard gas and the gas to be measured are easily separated, and can be made in a compact form. Which form is employed, namely, whether the standard electrodes (15A, 15B) are formed inside or outside of the solid electrolytes 11 and 21 may be determined by the practical conditions of how the introduction of the gas to be measured and the standard gas is carried out. The section of the solid electrolytes 11 and 21 and the bottomed holes 12A and 12B may not be circular as far as it is cylindrical, and may be of various shapes such as quadrilateral, polygon, and oval.

Figure 5:
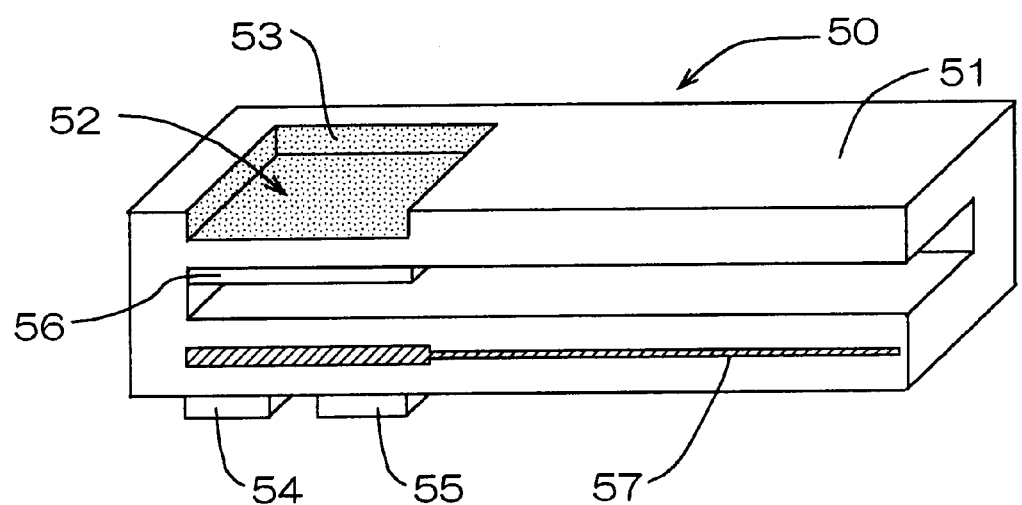
FIG. 5 is a sectional view showing still another embodiment of the CO sensor according to the present invention.

For example, a preferred structure is as of the CO sensor 50 shown in a sectional view of FIG. 5, namely, a solid electrolyte 51 is made in the form of a bottomed cylinder close to a quadrilateral, a recess 52 is formed on the outer surface of the bottom portion of the solid electrolyte 51, a CO sensing electrode 53 is formed in the recess 52, sensing electrodes 54 and 55 for measurement of $SO_2$ and $O_2$ as different gases are disposed on another outer surface of the bottom portion of the solid electrolyte 51, and a standard electrode 56 for measurement of CO, $SO_2$, and $O_2$ is formed on the inner surface of the bottom portion of the solid electrolyte 51. In the solid electrolyte 51 of the CO sensor 50 is disposed an electrical heater 57, and the CO sensor 50 can be kept at a given temperature and operated by this heater 57. Of course, such structure of the CO sensor of the present invention can also be applied to other gas sensors.

Method for making such cylindrical CO sensor will be explained taking the CO sensor 10 as an example. The solid electrolyte 11 can be easily made by cast molding, extrusion molding, injection molding and the like, and the formation of the bottomed holes can be carried out by processing of the green molded body, cutting of fired body of low strength, etc. depending on the method of the formation of the solid electrolyte. In the case of employing the injection molding, a solid electrolyte of a given shape including the bottomed holes can be obtained at the stage of molding without subjecting to after-processing. The resulting molded body or the like is fired, and connection of the electrodes is carried out in the same manner as for the CO sensor 1 shown in FIG. 1, for example, by coating a paste containing the electrode material at the position to be provided with electrode and pressing a mesh of electrode material, followed by baking. Thus, the CO sensor 10 can be made.

For the formation of CO sensing electrode 16 in the CO sensor 10, a method of using an organic metal solution containing Au or components of an Au alloy and/or components of the solid electrolyte is also simple and preferred. That is, for the formation of electrode in the inside of the bottomed hole 12A, the following method is possible, namely, after the organic metal solution is poured into the bottomed hole 12A, excess solution is sucked out by a dropping pipet, a cylinder or the like to coat the inner surface of the bottomed hole 12A with the solution, and, thereafter, the coat is dried and fired to form the CO sensing electrode 16. In this case, the lead wire may be temporarily fixed on the solid electrolyte 11, and a part of the lead wire may be immersed in the organic metal solution, fired and baked. Of course, the CO sensing electrode 53 can also be similarly formed in the recess 52 in the CO sensor 50 shown in FIG. 5.

Furthermore, like the aforementioned CO sensor 1, the CO sensor 10 has the structure of separating the gas to be measured and the standard gas to constitute a concentration cell and, hence, the standard electrode 15 can be made of the same components as of the CO sensing electrode 16. In this case, for the formation of an electrode at the outer surface of the bottom portion of the solid electrolyte 11, the bottom portion of the solid electrolyte 11 is immersed in said organic metal solution, and then taken out and dried, whereby a uniform electrode film can be formed. By such a simple method suitable for the shape of the CO sensor, not only the production cost can be reduced, but also the quality can be maintained constant.

As for the $SO_2$ sensing electrode 17, there can be similarly used an organic metal solution which contains Au or components of an Au alloy and glass components and precipitates glass at the time of firing. Further, the standard electrode 15 can also be formed using an organic metal solution of Pt. Of course, such method for the formation of electrodes using an organic metal solution can be applied to the formation of the CO sensor 1 shown in FIG. 1.

Next, a method of measurement using the CO sensor 10 will be explained. Since a CO reference electrode 18 is provided in the CO sensor 10, in addition to the above-mentioned measuring method by the CO sensor 1, mention may be made of a method which comprises measuring a CO concentration by measuring the change of electromotive force between the CO sensing electrode 16 and the CO reference electrode 18 caused by adsorption/oxidation of CO when a constant electric current is passed between the CO sensing electrode 16 and the standard electrode 15 (for measurement of CO), and measuring an $SO_2$ concentration by measuring the change of electromotive force caused by adsorption/oxidation of $SO_2$ when a constant electric current is passed between the $SO_2$ sensing electrode 17 and the standard electrode 15 (for measurement of $SO_2$), and then correcting the CO concentration with the $SO_2$ concentration. When an $SO_2$ reference electrode is also provided, the $SO_2$ concentration can be measured by measuring the change of electromotive force between the $SO_2$ sensing electrode 17 and the $SO_2$ reference electrode caused by adsorption/oxidation of $SO_2$ when a constant electric current is passed between the $SO_2$ sensing electrode 17 and the standard electrode 15 (for measurement of $SO_2$).

Furthermore, measurement of a precise CO concentration can be performed by measuring the CO concentration by measuring a current value passing between the CO sensing electrode 16 and the CO reference electrode 18 due to oxidation of CO when a constant voltage is kept between the CO sensing electrode 16 and the standard electrode 15 (for measurement of CO), and measuring the $SO_2$ concentration by measuring a current value passing due to oxidation reaction of $SO_2$ when a constant voltage is kept between the $SO_2$ sensing electrode 17 and the standard electrode 15 (for measurement of $SO_2$), and correcting the CO measured value with the $SO_2$ measured value. In this case, when an $SO_2$ reference electrode is further provided, it is preferred to measure the $SO_2$ concentration by measuring the current value between the $SO_2$ sensing electrode 17 and the $SO_2$ reference electrode.

Next, still another embodiment of the CO sensor of the present invention will be explained.

Figure 6:
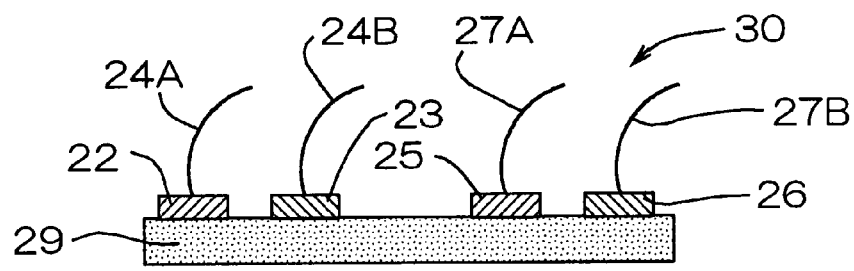
FIG. 6 is a sectional view showing still another embodiment of the CO sensor according to the present invention.

In the CO sensor 30 shown in FIG. 6, a CO standard electrode 22 and a CO sensing electrode 23, and an $SO_2$ standard electrode 25 and an $SO_2$ sensing electrode 26 are provided on the same surface of a solid electrolyte 29, Pt lead wires 24A and 27A are connected to the respective standard electrodes 22 and 25, and Au lead wires 24B and 27B are connected to the respective sensing electrodes 23 and 26. The standard electrodes 22 and 25 are suitably formed of Pt electrodes, the CO sensing electrode 23 is suitably formed of an electrode comprising Au or an Au alloy, or a cermet electrode comprising a mixture of Au or an Au alloy and the solid electrolyte, and the $SO_2$ sensing electrode 26 is suitably formed of an electrode comprising Au or an Au alloy and a glass component.

In this case, an electromotive force produced by the difference in the electrode reaction on the CO sensing electrode 23 and on the CO standard electrode 22 is measured, and an electromotive force produced by the difference in the electrode reaction on the $SO_2$ sensing electrode 26 and on the $SO_2$ standard electrode 25, and thus the CO concentration in the gas to be measured can be measured with correcting the CO concentration with the $SO_2$ concentration. Therefore, no standard gas is needed, and the whole of the CO sensor 30 is disposed in the atmosphere of the gas to be measured. The shape of the solid electrolyte 29 is not limited to a plate, but may be cylindrical, rod-like and others.

Figure 7:
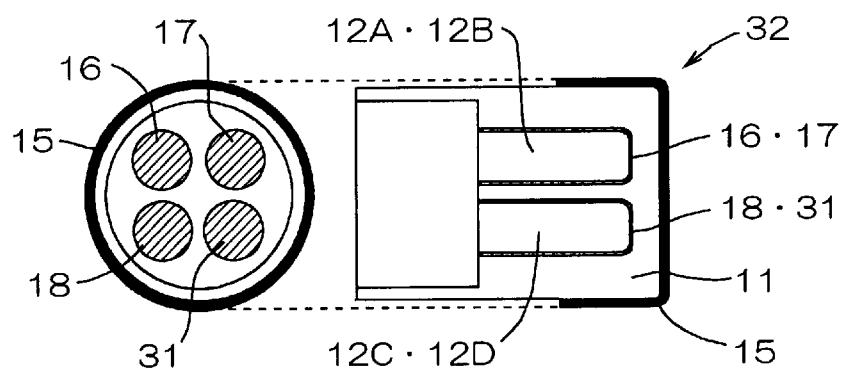
FIG. 7 is a sectional view showing an embodiment of the CO sensor according to the present invention in which an $O_2$ electrode is provided.

Next, in the present invention, when a sensing electrode and/or a standard electrode are provided so that oxygen as another one of the different gases can be measured, the measurement precision can be further improved and this is preferred. FIG. 7 shows a CO sensor 32 comprising the CO sensor 10 shown in FIG. 2 in which a bottomed hole 12D is additionally formed in the CO sensor 10 shown in FIG. 2, a sensing electrode 31 for measurement of $O_2$ (hereinafter referred to as "$O_2$ sensing electrode") is formed on the inner surface of the bottomed hole 12D, and thus an $O_2$ concentration can be simultaneously measured in addition to the CO concentration and the $SO_2$ concentration. In the CO sensor 32, the standard electrode 15 also functions as an $O_2$ standard electrode.

In this way, both the CO concentration and the $SO_2$ concentration are corrected using the result of the measurement of the $O_2$ concentration so as to exclude the influence by the reaction of $O_2$ at the respective electrodes, and the more precise CO concentration can be measured by further correcting the corrected CO concentration with the corrected $SO_2$ concentration.

Since the standard electrode 15 (for measurement of $O_2$) and the $O_2$ sensing electrode 31 in the CO sensor 32 are basically the same as an $O_2$ sensor, as the electrode material there can be suitably used a porous Pt electrode used for conventionally known electrode of zirconia $O_2$ sensor. Furthermore, methods for the formation of the standard electrode 15 (for measurement of $O_2$) and the $O_2$ sensing electrode 31, and methods for the connection of lead wires (not shown) to these electrodes can be carried out in the same manner as for the standard electrodes 2 and 4, and others in the CO sensor 1 mentioned above. A Pt wire is preferred as the lead wire connected to the electrodes for measurement of $O_2$. Of course, the embodiment of the CO sensor 32 can also be applied to the plate sensor shown in FIG. 1, and the CO standard electrode and the $O_2$ standard electrode may be formed as separate electrodes.

Figure 8:
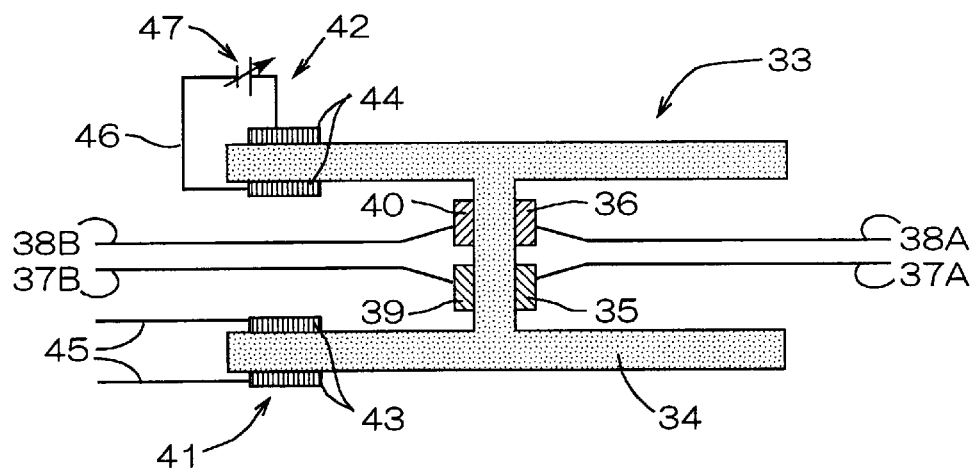
FIG. 8 is a sectional view showing an embodiment of the CO sensor according to the present invention in which an $O_2$ pump is provided.

FIG. 8 shows a CO sensor 33 comprising an H-shaped solid electrolyte 34 having two recesses. One of the recesses contacts with the atmosphere of the standard gas, in which a CO standard electrode 35 and an $SO_2$ standard electrode 36 which comprise porous Pt are provided on the bottom, and Pt lead wires 37A and 38A are connected to the standard electrodes 35 and 36, respectively. Another recess contacts with the atmosphere of the gas to be measured, in which a CO sensing electrode 39 comprising Au or an Au alloy and an $SO_2$ sensing electrode 40 comprising Au or an Au alloy and a glass component are provided on the bottom, and Au lead wires 37B and 38B are connected to the sensing electrodes 39 and 40, respectively.

In addition, on the side wall of the recess are provided an $O_2$ sensor 41 and an $O_2$ pump cell 42, and one of the electrodes 43 of the $O_2$ sensor 41 and one of the electrodes 44 of the $O_2$ pump cell 42 are formed on the inside of the recess, and another of the respective electrodes are formed on the outside of the recess, and all of these electrodes contact with the atmosphere of the gas to be measured. Here, the electrode 44 of the 02 pump cell preferably has the property not to oxidize CO and $SO_2$, and an electrode of an electrically conductive metal oxide such as lanthanum manganite ($LaMnO_3$) is suitably used. As lead wires 45 and 46 connected to the respective electrodes 43 and 44, Pt wires are suitably used, but since the electrode 44 is a ceramics electrode, lead wire 46 cannot be directly connected thereto by welding. Therefore, generally used is a method of metallizing the surface of the electrode 44 and then connecting the lead wire 46 thereto by baking.

By employing such structure, the $O_2$ pump cell 42 can be driven by controlling a potentiostat 47 by the $O_2$ sensor 41 so that $O_2$ concentration in the atmosphere of the gas to be measured is always constant. Accordingly, $O_2$ concentration in the gas to be measured is always kept constant in the vicinity of the CO sensing electrode 39 and the $SO_2$ sensing electrode 40, and hence measurements of CO and $SO_2$ can be performed with easily excluding the influence by $O_2$ exerted at the CO sensing electrode 39 and the $SO_2$ sensing electrode, and, as a result, further enhancement of measurement precision can be attained. The $O_2$ sensor 41 and $O_2$ pump cell 42 can also be formed in the cylindrical CO sensor 10 and others.

Figure 9:
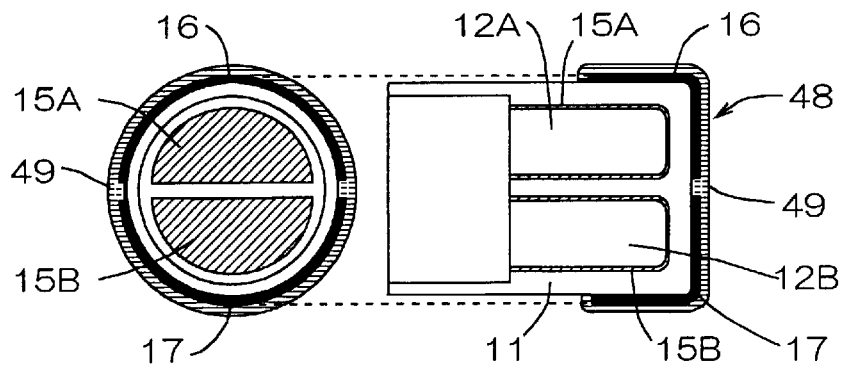
FIG. 9 is a sectional view showing an embodiment of the CO sensor according to the present invention in which a gas diffusion regulating layer is provided.

FIG. 9 shows a CO sensor 48 which has a gas diffusion regulating layer 49 provided on the surface of the CO sensing electrode 16 and the $SO_2$ sensing electrode 17 in the embodiment shown in FIG. 4, namely, the CO sensor 20. This gas diffusion regulating layer 49 can inhibit a combustible gas other than CO and $SO_2$, for example, a combustible gas of high molecular weight, such as a hydrocarbon, e.g., propane or butane, from diffusing to and contacting with the surface of the sensing electrodes 16 and 17. By providing such gas diffusion regulating layer 49, selectivity for CO and $SO_2$ in the sensor of the present invention can be improved.

Specifically, a zeolite film or the like is used as the layer, and the layer can be formed by lamination on the surface of the sensing electrodes 16 and 17 by dipping or the like, or after the sensing electrodes 16 and 17 are formed on the solid electrolyte 11, the layer can be formed by a method such as screen printing or sputtering. Of course, the gas diffusion regulating layer 49 can be applied to all of the embodiments mentioned above, and it may be formed on only either one of the CO sensing electrode or the $SO_2$ sensing electrode.

Figure 10:
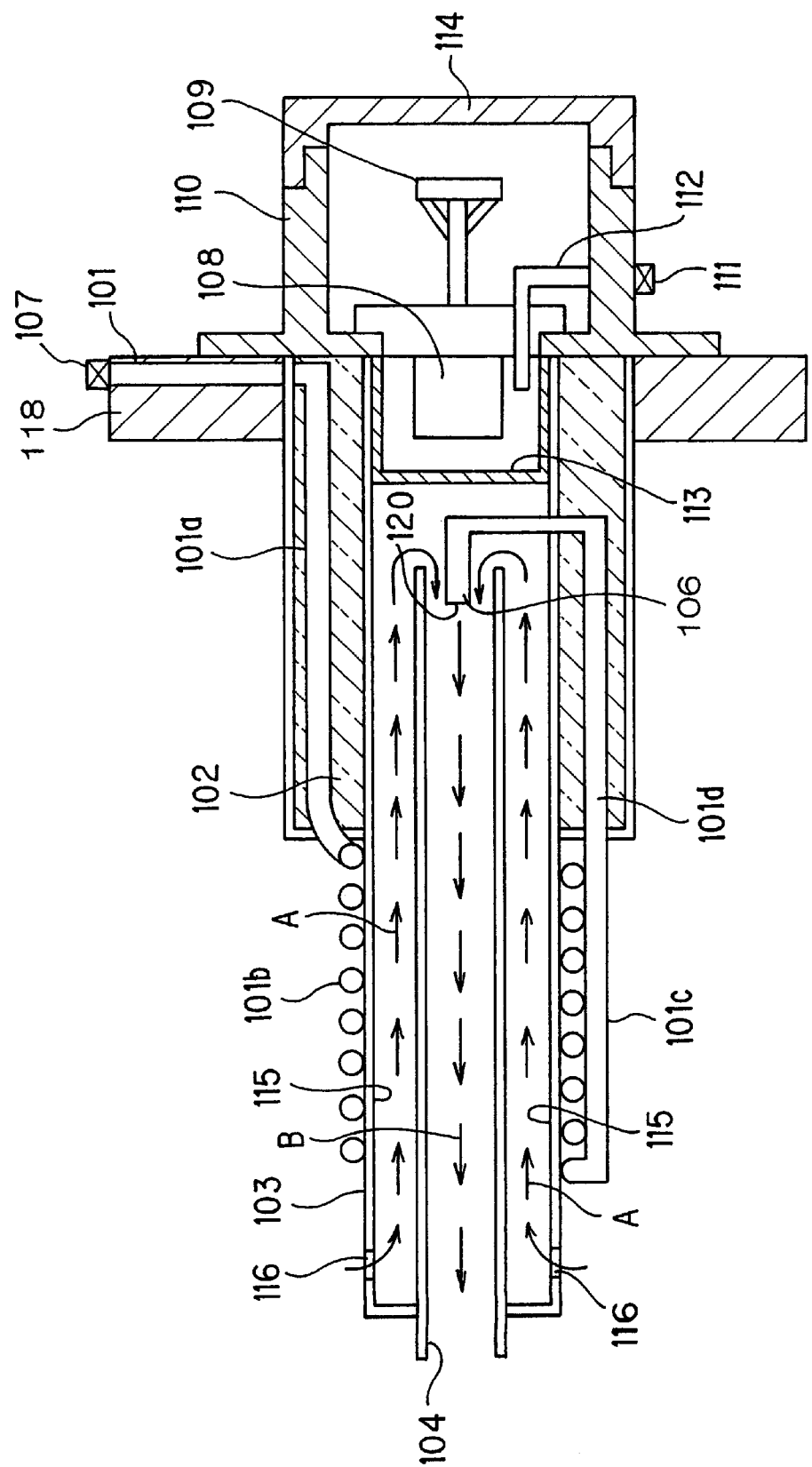
FIG. 10 is a sectional view of a CO measuring device on which the CO sensor according to the present invention is mounted.

FIG. 10 is a schematic view of a basic structure of a direct coupling type CO measurement apparatus having the CO sensor shown in FIG. 1. This apparatus is basically composed of a sensor case 110 having a sensor device mounting portion 118, a sensor cover 114 detachably mounted on the sensor case 110, a CO sensor 108 of the present invention disposed in the sensor box, a fastening base 109 for fastening the sensor 108, a standard gas feed pipe 112, a filter 113 comprising a porous ceramics provided in front of the sensor 108, a measurement gas sampling tube 103 having a double structure, and an ejector gas feed pipe 101.

The measurement gas sampling pipe 103 has a double structure in which a measurement gas sampling path 115 is formed on the outer peripheral side and a measurement gas discharge path 104 is formed on the inner side. An ejector gas feed port 107 is provided at one end of the ejector gas feed pipe 101. This ejector gas feed pipe 101 first passes through a heat insulator 102 as shown by 101*a*; thereafter reaches an exposed ejector gas feed pipe portion 101*b* in the form of a spiral wound around the outer periphery of the measurement gas sampling tube 103 in the exposed state; then is connected to an exposed linear ejector gas feed pipe portion 101*c*; again passes through the heat insulator 102 as shown by 101*d*; is exposed inside the measurement gas sampling tube 103; and is connected to an ejector 106.

When an ejector gas is fed from the ejector feed port 107, this ejector gas passes through the embedded portion 101*a* in the heat insulator 102, the exposed portions 101*b* and 101*c*, and the embedded portion 101*d* in the heat insulator 102 in this order, and is blown out of an ejector blow port 120 of the ejector 106. Thus, a negative pressure is generated around the ejector 106 to produce a convection, and, as a result, the measurement gas is sampled from the outside of this device by the sampling port 116, flows through the measurement gas sampling path 115 as indicated by arrows A, is reversed and flows the measurement gas discharge path 104 as indicated by arrows B, and is again discharged to the outside of the device. During this course, CO in the measurement gas is measured by the sensor 108.

As mentioned above, according to the CO sensors of the present invention and the method of using the sensors, $SO_2$ concentration can also be simultaneously measured when CO concentration in exhaustion gas and others is measured, and, hence, the CO concentration can be precisely measured with excluding the influence of the reaction in which $SO_2$ participates at the sensing electrode for measurement of CO. Furthermore, since measurement of the CO concentration and that of the $SO_2$ concentration by one sensor can be performed by one sensor, the sensor can be easily disposed at various places. Moreover, by additionally providing a function to measure $O_2$ concentration, more precise measurement of the CO concentration and the $SO_2$ concentration becomes possible, whereby measurement precision of CO can be further improved, and by further providing an $O_2$ pump, the influence of the $O_2$ concentration on the CO concentration measured value and the $SO_2$ concentration measured value can be markedly reduced. In case the CO sensor has a structure of bottomed cylindrical shape, the measurement gas and the standard gas can be easily separated. Furthermore, according to the method for making the CO sensor of the present invention; uniform electrodes can be simply formed by using an organic metal solution, and productivity can be improved.

What is claimed is:

1. A sensor for sensing carbon monoxide and sulfur dioxide, comprising a solid electrolyte having oxygen ion conductivity, and a standard electrode and a sensing electrode for measurement of carbon monoxide, the carbon monoxide measurement sensing electrode comprising gold or a gold alloy, and a standard electrode and a sensing electrode for measurement of sulfur dioxide, said respective standard electrodes and sensing electrodes being formed on at least a part of the surface of the solid electrolyte.

2. A sensor according to claim 1, wherein the sensing electrode for measurement of carbon monoxide is a cermet electrode comprising ceramic and a metal wherein the metal comprises gold or a gold alloy and the ceramic comprises the same material as the solid electrolyte.

3. A sensor according to claim 1, wherein the sensing electrode for measurement of carbon monoxide, the standard electrode for measurement of carbon monoxide, or both are formed by coating an organic metal solution containing, at least one material selected from the group consisting of gold, a component of gold alloy and a component of the solid electrolyte, and firing the coating.

4. A sensor according to claim 1, wherein a reference electrode for measurement of carbon monoxide is additionally provided.

5. A sensor according to claim 1, wherein the sensing electrode for measurement of sulfur dioxide comprises a metal component of gold or a gold alloy and a glass component in combination.

6. A sensor according to claim 5, wherein a reference electrode for measurement of sulfur dioxide is additionally provided.

7. A sensor according to claim 6, wherein one electrode is commonly used as the standard electrode for measurement of carbon monoxide and the standard electrode for measurement of sulfur dioxide.

8. A sensor according to claim 1, further comprising a standard electrode and a sensing electrode for measurement of oxygen.

9. A sensor according to claim 1, wherein a gas diffusion regulating layer is provided on the surface of the sensing electrode(s) for measurement of carbon monoxide and/or sulfur dioxide.

10. A sensor according to claim 1, further comprising means for providing a measurement gas atmosphere to be measured in contact with the respective sensing electrodes and an oxygen pump cell for controlling the oxygen concentration in the measurement gas atmosphere to be measured.

11. A sensor according to claim 10, wherein the electrode of the oxygen pump cell comprises a metal oxide.

12. A sensor according to claim 1, wherein the solid electrolyte comprises zirconium oxide and a stabilizer.

13. A sensor according to claim 12, wherein the stabilizer contained in the solid electrolyte contains at least one compound selected from magnesium oxide, calcium oxide, yttrium oxide, cerium oxide, scandium oxide, and rare earth metal oxides.

14. A sensor according to claim 13, wherein an electric heater is disposed in the solid electrolyte.

15. A sensor according to claim 1, wherein the sensing electrode for measurement of carbon monoxide is formed in a recess provided on the outer surface of the bottom portion of the solid electrolyte having a bottomed cylindrical shape, the sensing electrode for measurement of sulfur dioxide is formed on the outer surface of the bottom portion of the solid electrolyte, and the standard electrode and any additional reference electrode for measurement of carbon monoxide and sulfur dioxide are formed on the inner surface of the bottom portion of the solid electrolyte.

16. A sensor according to claim 1, wherein the solid electrolyte has a bottom cylindrical shape, at least two bottomed holes are formed in the inner bottom portion of the solid electrolyte, and at least one electrode is formed on the outer surface of the bottom portion of the solid electrolyte and at least one electrode is formed on each inner surface of the bottomed boles, respectively.

17. A sensor according to claim 16, wherein the sensing electrode for measurement of carbon monoxide and a sensing electrode for measurement of sulfur dioxide are formed on the outer surface of the bottom portion of the solid electrolyte, and the standard electrode and any additional reference electrode are formed on each inner surface of the bottomed holes, respectively. formed on the outer surface of the bottom portion of the solid electrolyte, and the sensing electrode for measurement of carbon monoxide and a sensing electrode for measurement of a gas other than carbon monoxide are formed on each inner surface of the bottomed holes, respectively.

18. A sensor according to claim 16, wherein the standard electrode and any additional reference electrode are formed on the outer surface of the bottom portion of the solid electrolyte, and the sensing electrode for measurement of carbon monoxide and a sensing electrode for measurement of sulfur dioxide are formed on each inner surface of the bottomed holes, respectively.

19. A sensor according to claim 1, wherein the solid electrolyte is a rod-like shape, at least two bottomed holes are formed in parallel to the lengthwise direction of the solid electrolyte, and at least one electrode is formed on the outer surface of the bottom portion of the solid electrolyte and at least one electrode is formed on each inner surface of the bottomed holes, respectively.

20. A sensor according to claim 19, wherein the sensing electrode for measurement of carbon monoxide and a sensing electrode for measurement of sulfur dioxide are formed on the outer surface of the bottom portion of the solid electrolyte, and the standard electrode and any additional reference electrode are formed on each inner surface of the bottomed holes, respectively.

21. A sensor according to claim 19, wherein the standard electrode and any additional reference electrode are formed on the outer surface of the bottom portion of the solid electrolyte, and the sensing electrode for measurement of carbon monoxide and a sensing electrode for measurement of sulfur dioxide are formed on each inner surface of the bottomed holes, respectively.

22. A combination sensor according to claim 1, further comprising a standard electrode and a sensing electrode for measurement of oxygen.

* * * * *